(12) United States Patent
Carnegie et al.

(10) Patent No.: US 6,966,234 B2
(45) Date of Patent: Nov. 22, 2005

(54) REAL-TIME MONITORING AND CONTROL OF RESERVOIR FLUID SAMPLE CAPTURE

(75) Inventors: Andrew J. Carnegie, Abu Dhabi (AE); Serkan Yilmaz, Ahwaz (IR)

(73) Assignee: Schlumberger Technology Corporation, Sugar Land, TX (US)

( * ) Notice: Subject to any disclaimer, the term of this patent is extended or adjusted under 35 U.S.C. 154(b) by 143 days.

(21) Appl. No.: 10/707,808

(22) Filed: Jan. 14, 2004

(65) Prior Publication Data

US 2005/0150287 A1 Jul. 14, 2005

(51) Int. Cl.7 .............................................. G01N 1/00
(52) U.S. Cl. .................. 73/863.21; 73/152.24
(58) Field of Search ........................ 73/863.21, 864.34, 73/864.35, 152.23, 152.24, 152.25, 152.26; 166/264

(56) References Cited

U.S. PATENT DOCUMENTS

| | | | |
|---|---|---|---|
| 3,912,456 A | * 10/1975 | Young | 436/47 |
| 4,860,581 A | * 8/1989 | Zimmerman et al. | 73/152.26 |
| 6,058,773 A | * 5/2000 | Zimmerman et al. | 73/152.24 |
| 6,706,094 B2 | * 3/2004 | Browne | 95/241 |

* cited by examiner

*Primary Examiner*—Robert Raevis

(74) *Attorney, Agent, or Firm*—Brigitte L. Echols

(57) ABSTRACT

A method of sampling reservoir fluid includes establishing communication between a reservoir and an entry port of a flow line disposed in a borehole penetrating the reservoir. The method includes separating fluid received in the entry port into individual fluid components and sequentially flowing slugs of each individual fluid component along the flow line, observing the slugs as they move along the flow line in order to determine the composition of the slugs, estimating when a desired slug containing a desired fluid component would be in the vicinity of a sample chamber in the flow line, and opening the sample chamber to capture the desired slug when the desired slug is in the vicinity of the sample chamber. The method also includes checking that the sample chambers open and close successfully. Finally, the method further includes creating an accurate record of events, which can then be used to audit the sampling process.

14 Claims, 5 Drawing Sheets

US 6,966,234 B2

REAL-TIME MONITORING AND CONTROL OF RESERVOIR FLUID SAMPLE CAPTURE

BACKGROUND OF INVENTION

The invention relates to methods and apparatus for sampling reservoir fluid.

A reservoir is a rock formation in which fluids, e.g., hydrocarbons such as oil and natural gas and water, have accumulated. Due to gravitational forces, the fluids in the reservoir are segregated according to their densities, with the lighter fluid towards the top of the reservoir and the heavier fluid towards the bottom of the reservoir. One of the main objectives of formation testing is to obtain representative samples of the reservoir fluid. Commonly, reservoir fluid is sampled using a formation tester, such as the Modular Formation Dynamics Tester (MDT), available from Schlumberger Technology Corporation, Houston, Tex. In practice, the formation tester is conveyed, generally on the end of a wireline, to a desired depth in a borehole drilled through the formation. The formation tester includes a probe that can be set against the borehole wall, allowing reservoir fluid to be drawn into a flow line in the formation tester. The formation tester also includes a pump and one or more sample chambers. Typically, optical fluid analyzers are inserted into the flow line of the formation tester to monitor the fluid(s) flowing in various locations of interest. For example, an optical analyzer is often run directly above the probe to monitor the type of fluid entering the flow line.

Initially, the fluid drawn into the flow line is a mixture of reservoir fluid and mud filtrate. To obtain a sufficiently high quality fluid sample, a cleanup step in which mud filtrate is purged from the flow line is performed. This step involves pumping fluid through the flow line and out into the well. As pumping continues, more and more of the reservoir fluid is consumed around the inlet of the probe. Eventually, a fluid mixture that is more representative of the reservoir fluid starts to enter the flow line. Optical fluid analyzers are used to monitor the content of the fluid entering the flow line and how the fluid proceeds through the tool. When the mud filtrate content of the fluid entering the flow line is reduced to an acceptable level, the sample chamber is opened and fluid in the flow line is pumped into the sample chamber. Usually, the following ancillary objectives are set for this step: (1) that a certain minimum volume of reservoir fluid be captured, and (2) that the reservoir fluid captured be single hydrocarbon phase, e.g., oil phase or gas phase, but not both. Finally, the sample chamber is closed and returned to the surface.

In practice, there is only a certain maximum time allowed before the cleanup step must be terminated. Therefore, there is no guarantee that the fluid mixture in the flow line is adequately decontaminated prior to being captured in the sample chamber. Further, the sample chamber may be returned to the surface without a sample, e.g., because the sample chamber was not opened successfully. Further, the sample chamber may be returned to the surface unclosed, e.g., because the sample chamber was not successfully closed after the fluid sample was collected. In this case, the content of the sample chamber may be lost or exposed to contaminants or undergo a phase change as it is returned to the surface. Prior to the present invention, the inventors are not aware of methods for verifying in real-time that the three steps described above, i.e., cleanup, sample capture, and sample chamber closing, are successfully accomplished before the sample chamber is retrieved to the surface.

From the foregoing, there is desired a method of assuring quality fluid sample capture from a reservoir.

SUMMARY OF INVENTION

In one aspect, the invention relates to a method of sampling reservoir fluid which comprises establishing communication between a reservoir and an entry port of a flow line disposed in a borehole penetrating the reservoir, separating fluid received in the entry port into individual fluid components and sequentially flowing slugs of each individual fluid component along the flow line, observing the slugs as they move along the flow line in order to determine the composition of the slugs, estimating when a desired slug containing a sufficient volume of desired fluid component would be in the vicinity of a sample chamber in the flow line, and opening the sample chamber to capture the desired slug when the desired slug is in the vicinity of the sample chamber.

In another aspect, the invention relates to a system for sampling reservoir fluid which comprises a tool body having a flow line with an entry port and an exit port and being adapted to be suspended in a borehole penetrating a reservoir. The system includes a fluid separator installed in the flow line for separating fluid received from the entry port into individual fluid components and sequentially outputting slugs of each individual fluid into the flow line. The system includes a fluid analyzer installed in the flow line downstream of the fluid separator for determining the composition of the slugs as they move along the flow line. The system includes at least one sample chamber in the flow line downstream of the fluid analyzer for capturing a desired slug containing a desired fluid component.

Other features and advantages of the invention will be apparent from the following description and the appended claims.

DETAILED DESCRIPTION

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

Figure 1:
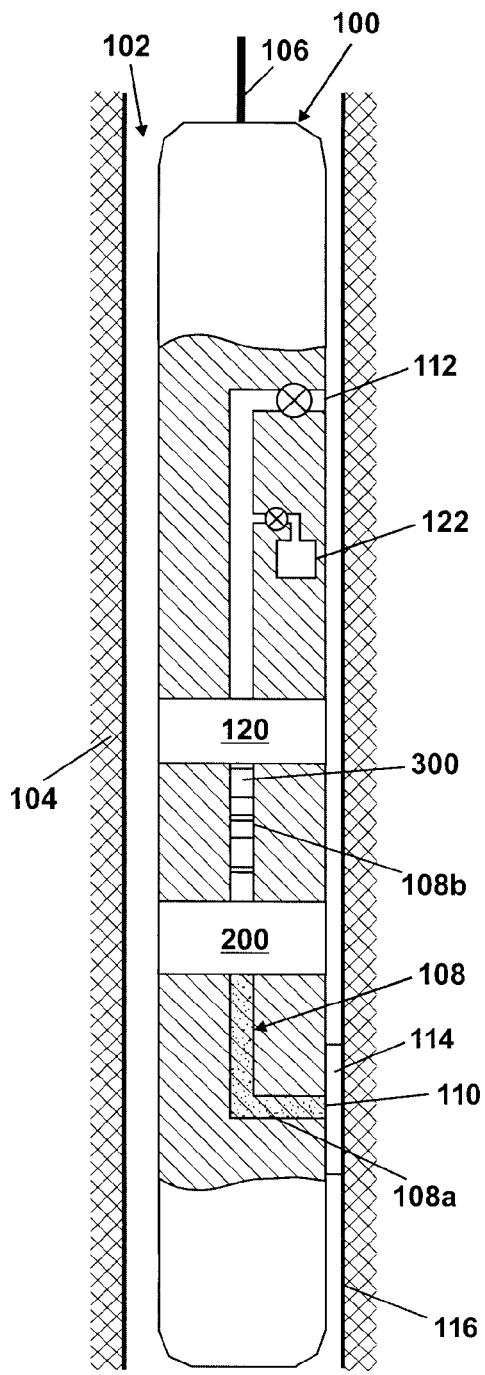
FIG. 1 is a simplified diagram of a downhole tool for sampling reservoir fluid in accordance with one embodiment of the invention.

FIG. 1 shows a simplified diagram of a downhole tool 100 for sampling reservoir fluid in accordance with one embodiment of the invention. The downhole tool 100 is conveyed to a selected depth in a borehole 102 drilled through a rock formation 104 using, for example, a wireline 106. The downhole tool 100 includes a flow line 108 having an entry port 110 and an exit port 112. A probe assembly 114, such as the Single-Probe Module or Dual-Probe Module included in the Schlumberger MDT or described in U.S. Pat. Nos. 4,860,581 and 6,058,773, both assigned to Schlumberger Technology Corporation, may be mounted at the entry port 110. The probe assembly 114 can be extended to and set against the borehole wall 116 so that reservoir fluid in the formation 104 can be drawn into the entry port 110. Although not shown, a packer assembly, such as the Dual-Packer Module included in the Schlumberger MDT or described in U.S. Pat. No. 4,860,581, may be installed below the probe assembly 114. The packer assembly may be inflated against the borehole wall 116 to isolate an interval of the formation 104 to be tested.

The downhole tool 100 includes a pump 200, such as the Pump-Out module included in the Schlumberger MDT or described in U.S. Pat. Nos. 4,860,581 and 6,058,773, installed above the probe assembly 114. In the following discussion, the portion of the flow line 108 between the entry port 110 and the pump 200 will be referred to as the inlet flow line 108a, and the portion of the flow line 108 between the pump 200 and the exit port 112 will be referred to as the outlet flow line 108b. The downhole tool 100 further includes a fluid type analyzer 120, such as the Live Fluid Analyzer (LFA) included in the Schlumberger MDT, installed above the pump 200. The fluid type analyzer 120 analyzes the output of the pump 200 as opposed to the input to the pump 200 as done in conventional formation testing. The downhole tool 100 further includes at least one sample chamber 122, such as the Modular Sample Chamber, Multi-Sample module, or Single-Phase Multi-Sample Chamber included in the Schlumberger MDT. Other components necessary to make the downhole tool 100 fully functional, such as a power cartridge, which are not shown are within the purview of one skilled in the art. The wireline 106 may be used to transmit data to the surface.

In one embodiment, the pump 200 is a dual-displacement pump. The function of the dual-displacement pump 200 is two-fold. One function is to pump fluid into or out of the flow line 108 or into or out of the sample chamber 122. The second function is to separate a fluid mixture received in the inlet flow line 108a into individual fluids according to the density of the individual fluids and then sequentially output slugs of these individual fluids into the outlet flow line 108b, where the slugs move like a train along the outlet flow 108b. In this way, a slug containing a desired fluid (such as a hydrocarbon) can be captured into the sample chamber 122 while slugs containing unwanted fluid (such as mud filtrate) can be allowed to exit the outlet flow line 108b through the exit port 112. The dual-displacement pump 200 can create trains of slugs of individual fluids in a predictable pattern because fluid separation occurs in each cycle of the pump. However, the invention is not limited to use of a dual-displacement pump as a fluid separator. In general, any device that can separate a fluid mixture into individual fluids and create slugs of these individual fluids in a predictable pattern can be used in the invention. An example of a down hole fluid separator is any chamber that has a significantly larger diameter than the diameter of the flow line 108. The chamber would be placed somewhere in the flow line 108 (before the fluid analyzer 120). The fluid mixture would enter the chamber from the flow line which is attached to the bottom of the chamber. Fluid phases of different density would segregate in the chamber, and the separated mixture would leave from the top of the chamber into the flow line. The segregation causes the fluids to leave as a train of slugs. It should be noted that if the fluid separator is not a pump, a pump would still be needed to pump fluid into and out of the flow line 108 or into and out of the sample chamber 122.

Figure 2B:
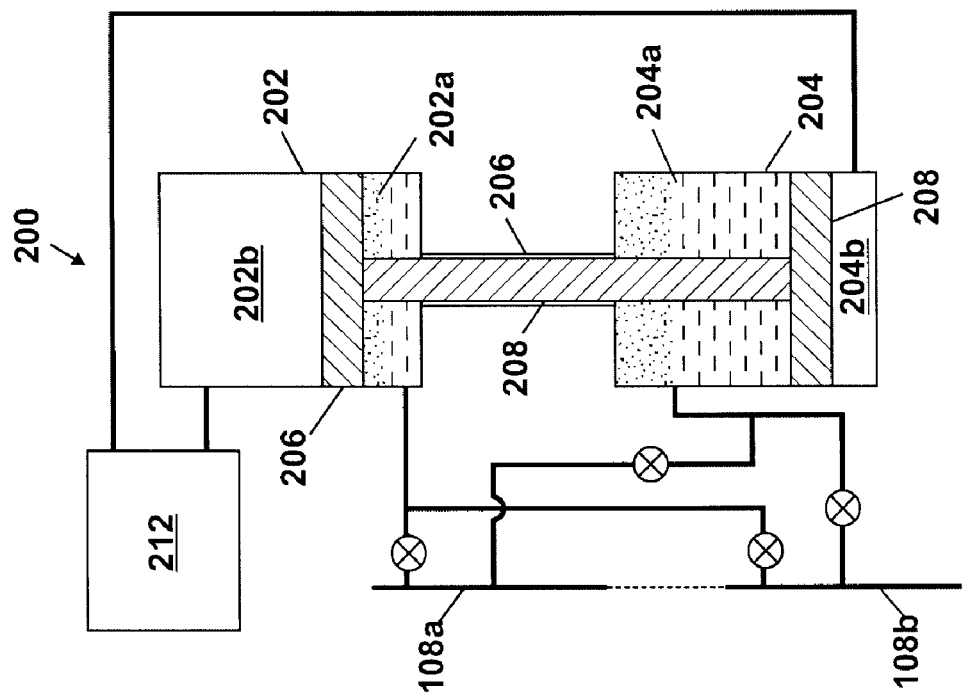
FIGS. 2A and 2B are schematic illustrations of a dual-displacement pump.
Figure 2A:
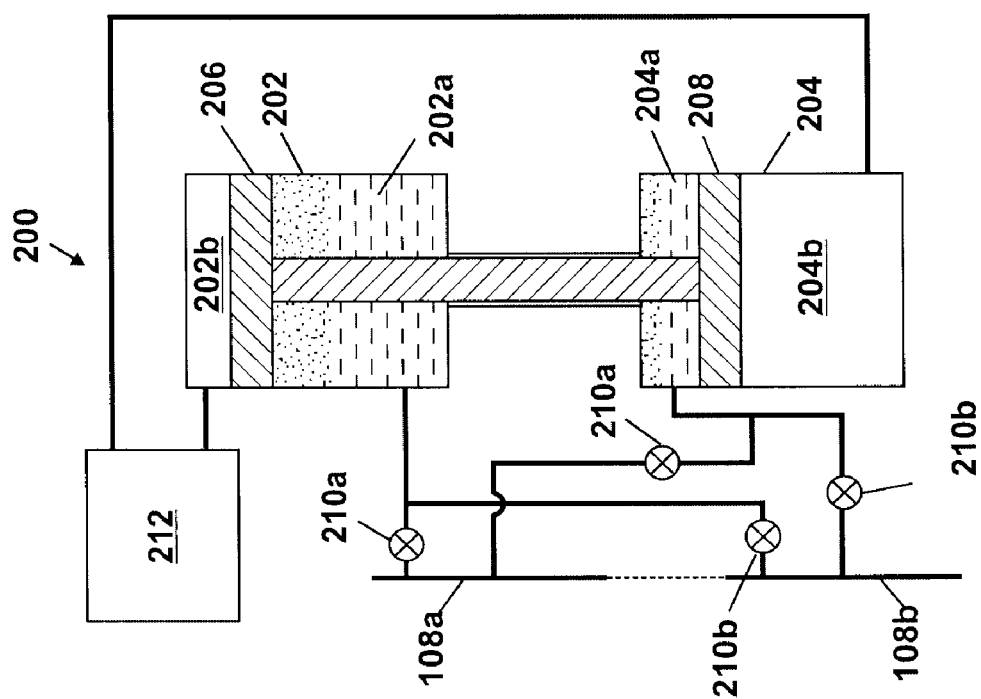

FIG. 2A shows the pump 200 configured as a dual-displacement pump. In this embodiment, the pump 200 includes hydraulic cylinders 202, 204. The pistons 206, 208 of the hydraulic cylinders 202, 204, respectively, are coupled together so that they move concurrently. The hydraulic cylinders 202, 204 have pump chambers 202a, 204a, which can be selectively connected to the inlet flow line 108a to receive fluid or the outlet flow line 108b to dispense fluid. Inlet check valves 210a and outlet check valves 210b control which of the flow lines 108a, 108b is in communication with the pump chambers 202a, 204a at any time. The hydraulic cylinders 202, 204 also have hydraulic fluid chambers 202b, 204b, which are in communication with a hydraulic fluid source 212. Hydraulic fluid is alternately supplied to the hydraulic fluid chambers 202b, 204b to either move the pistons 206, 208 downwardly (down-stroke) or upwardly (up-stroke). The dual-displacement pump arrangement eliminates refill dead time by refilling one of the hydraulic cylinders 202, 204 with fluid while the other hydraulic cylinder is dispensing fluid.

During the down-stroke cycle, hydraulic fluid is supplied to the hydraulic fluid chamber 202b, forcing the pistons 206, 208 to move downwardly. As the pistons 206, 208 move downwardly, slugs of fluids are dispensed from the pump chamber 202a into the outlet flow line 108b while the pump chamber 204a is filled with fluid from the inlet flow line 108a. The fluid admitted into the pump chamber 204a is usually a mixture of fluids, such as hydrocarbons, water, and mud filtrate. Due to gravity, the fluid in the pump chamber 204a separates into individual fluids, with the lighter fluid towards the top of the chamber and the heavier fluid towards the bottom of the chamber. To allow mud filtrate to form a distinct layer from hydrocarbons, the mud filtrate is preferably water-based as opposed to oil-based. During the up-stroke cycle, as shown in FIG. 2B, hydraulic fluid is supplied to the hydraulic fluid chamber 204b, forcing the pistons 206, 208 to move upwardly. As the pistons move upwardly, the separated fluids in the pump chamber 204a are dispensed into the outlet flow line 108b, one individual fluid at a time. The individual fluids are dispensed as slugs. While the pump chamber 204a is dispensing, the pump chamber 202a is filled with fluid from the inlet flow line 108a.

Figure 3:
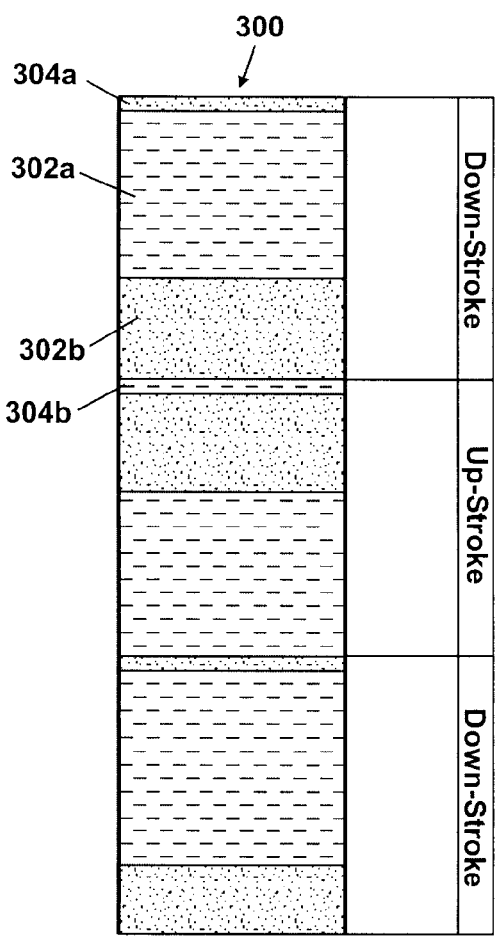
FIG. 3 shows an example of an output of the dual-displacement pump of FIGS. 2A and 2B.

Each cycle of the dual-displacement pump 200 results in fluid separation. Thus, slugs of individual fluids are continuously dispensed from the pump 200 into the outlet flow line 108b in a predictable manner. For illustrative purposes, FIG. 3 shows slugs, generally indicated at 300, leaving the pump. The pump stroke direction when the slugs 300 were produced is indicated in the figure. Two main volume slugs 302a, 302b, each main volume corresponding to an individual fluid, are shown for each pump stroke. At the beginning of each down-stroke and up-stroke of the pump is a dead volume slug 304a, 304b, respectively. The dead volume is the section of outlet flow line (108b in FIGS. 2A, 2B) between the port of each pump chamber (202a, 204a in FIGS. 2A, 2B) and the output check valve (210b in FIGS. 2A, 2B). The dead volume 304a at the beginning of each down-stroke contains the last fluid pumped out from the previous up-stroke of the pump. If the fluid in the pump chamber 202a contains gas, the dead volume 304a would be gas. The dead volume 304a can be a good indicator of whether any gas flows out of the pump, especially when there is very little gas flow.

Figure 4:
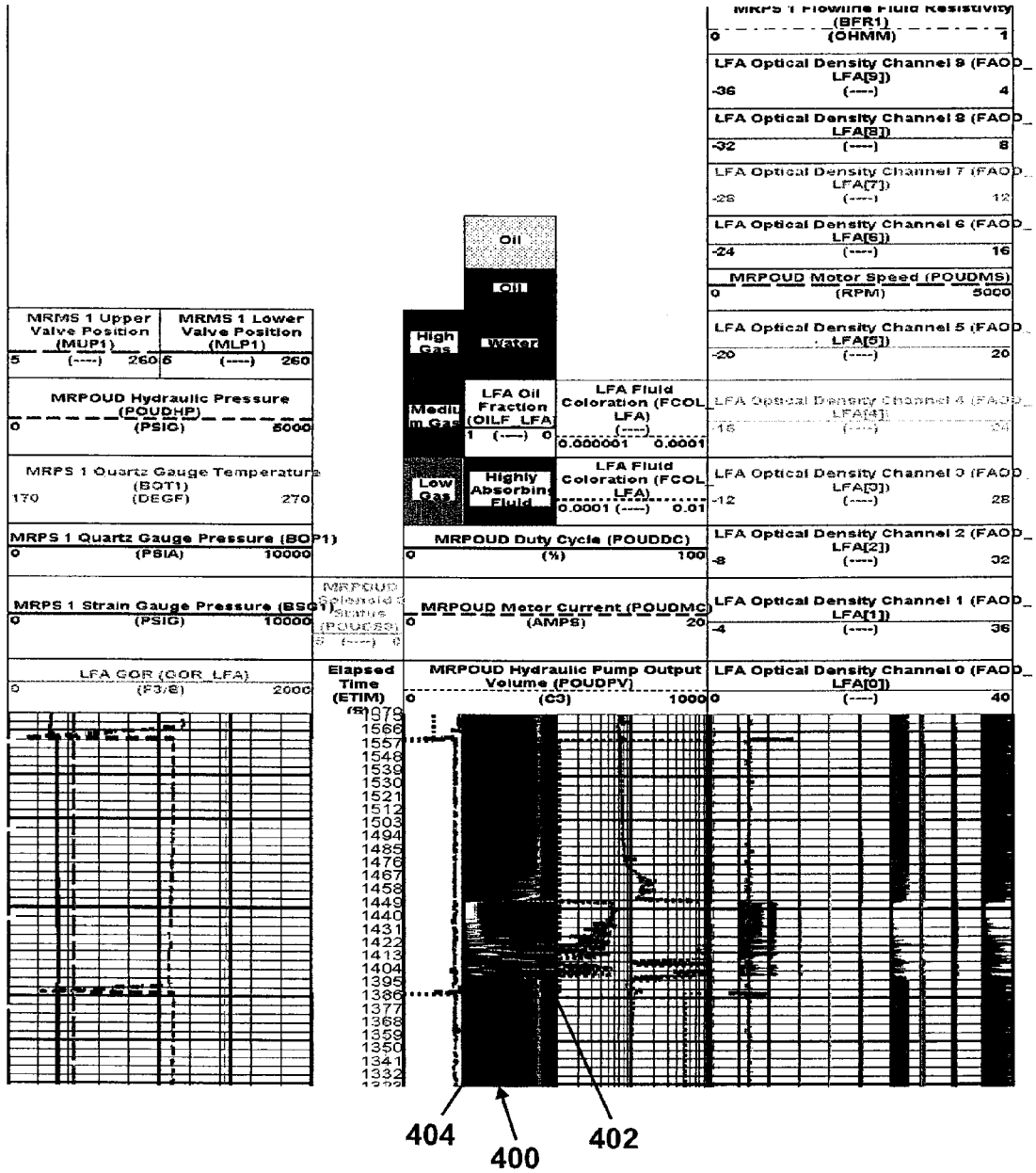
FIG. 4 shows flow line behavior before sample capture.

Returning to FIG. 1, since fluid leaves the pump 200 as slugs of individual fluids 300, an operator at the surface can advantageously time opening of the sample chamber 122 such that as much as possible of one of the slugs 300 containing a desired fluid can be captured. In order to do this, the operator needs to know when the slug containing the desired fluid is leaving the pump 200. This is accomplished by observing over a time period the pattern in which slugs are outputted from the pump. To do this, the slugs 300 leaving the pump 200 are passed through the fluid type analyzer 120. The fluid type analyzer 120 may include a gas detector, e.g., a gas refractometer, to distinguish between a liquid phase and a gas phase and/or a liquid detector, e.g., an optical absorption spectrometer, to distinguish between liquid and/or gas phases. As the slugs 300 pass through the fluid type analyzer 120, the fluid type analyzer 120 generates an output, such as an absorption spectra, that can be used to determine the composition of the slugs passing through it. FIG. 4 shows an example of flow (indicated at 400) detected by the fluid type analyzer 120 prior to sample capture. Oil slugs 402 and water slugs 404 are shown. Oil and water are reliably detected by their different absorption spectra. The fluid (slug) volume is shown as a function of time. By observing this output, the operator can predict when to expect a slug having a sufficient volume of a desired fluid component, e.g., oil.

Returning to FIG. 1, an operator at the surface monitors the output of the fluid type analyzer 120 and the pressure at the entry port 110 of the flow line 108, the hydraulic pressure of the pump 200, and the stroke direction of the pump 200. The operator uses this information to determine when to open the sample chamber 122 to capture the desired slug. The volumes of most types of sample chambers are significantly smaller than the volume of one pump stroke. Thus, it should be possible to capture enough low-contamination hydrocarbon slug into a sample chamber even when there is still significant amount of mud filtrate contamination. This capability will significantly shorten sampling times. The operator can time opening of the sample chamber 122 to avoid capturing as much as possible of any unwanted fluids. For example, if a single-phase oil sample is desired, and free gas is also slugging out of the pump 200, the operator can time opening and closing of the sample chamber 122 to avoid capturing the gas. The main and dead volumes in the fluid analyzer 120 output are observed to see if the slug leaving the pump is single phase or two phase. The dead volumes are observed to see if the slug leaving the pump contains free gas.

Fluid sampling involves establishing communication between the formation 104 and the entry port 110 of the flow line 108. Once communication is established between the formation 104 and the entry port 110, the pump 200 draws fluid into the inlet flow line 108a through the entry port 110 and sequentially dispenses slugs of individual fluids into the outlet flow line 108b. The slugs move in trains through the fluid analyzer 120. In general, the slugs move at the speed of the most viscous phase. As the slugs move through the fluid type analyzer 120, they are detected and analyzed by the fluid type analyzer 120. The operator monitors the output of the fluid type analyzer 120 to determine the fluid type of the slugs produced by the pump 200. From the output, the operator can predict when a slug having a desired fluid is leaving the pump 200. This also allows the operator to determine when to open the sample chamber 122 to capture the desired slug.

To capture the desired slug, the operator opens the sample chamber 122 and closes the exit port 112 of the flow line 108 at approximately the same time. Then, the operator starts pumping fluid through the flow line 108. If the exit port 112 is closed and the sample chamber 122 is successfully opened, the fluid in the flow line 108 will be diverted into the sample chamber 122. As soon as the sample chamber 122 becomes full, the pump 200 would experience increasing resistance and the hydraulic pressure of the pump 200 would increase noticeably. At the same time, flow from the formation would basically stop and the pressure at the entry port 110 would build up towards formation pressure. By observing the relationship between volume pumped into the sample chamber 122, hydraulic pressure of the pump 200, and the pressure of the fluid entering the flow line 108, it may be verified that the sample chamber 122 opened successfully and captured fluid pumped from the formation. For a good sample capture, there should be more than one pump stroke between opening of the sample chamber 122 and pressure up, i.e., when the hydraulic pressure of the pump 200 increases noticeably, and drawdown should remain constant. When trying to capture a single hydrocarbon phase, the sample chamber 122 should be opened somewhere during the pump down-stroke.

Figure 5:
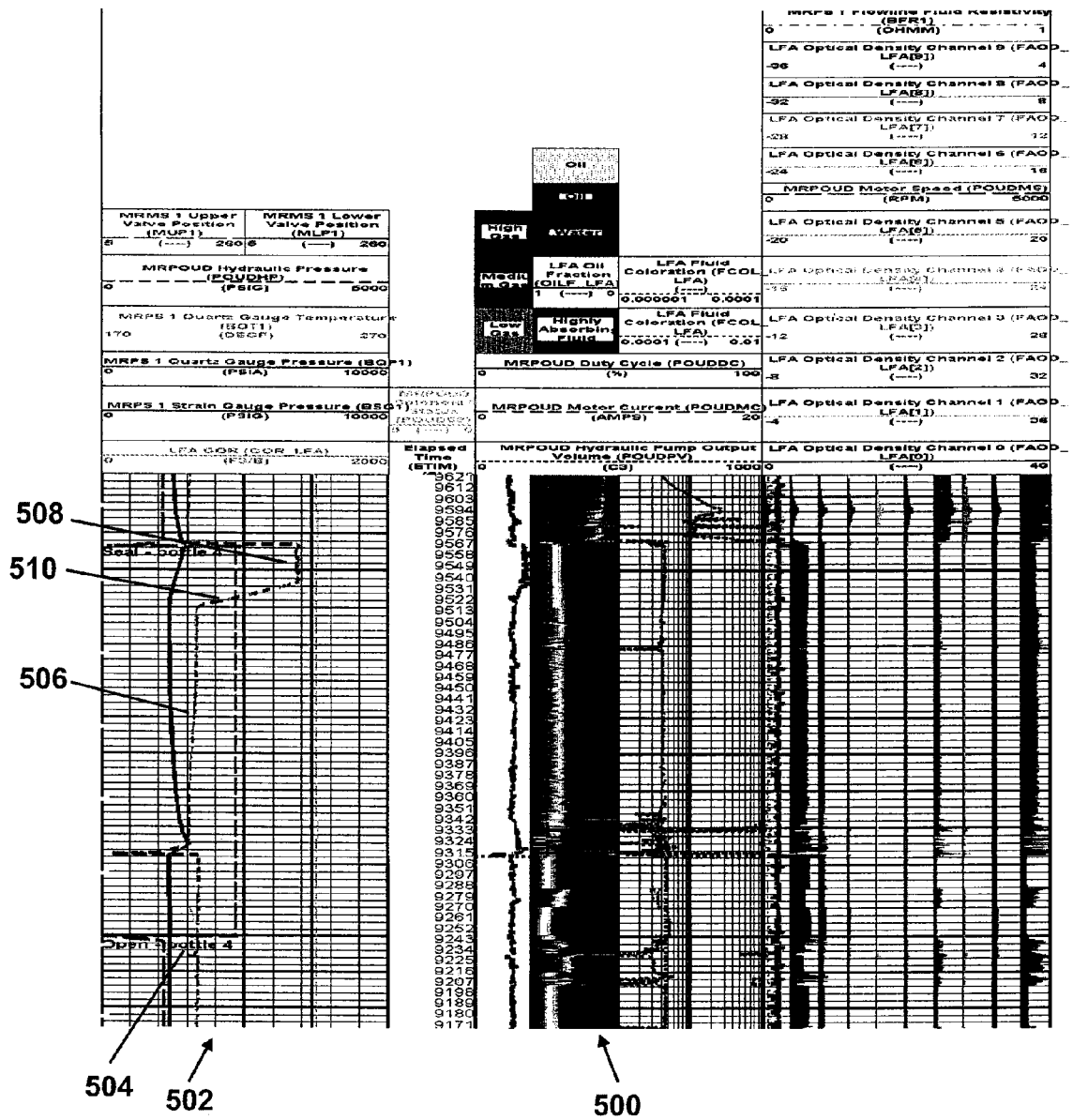
FIG. 5 shows flow line behavior after sample capture.
Figure 6:
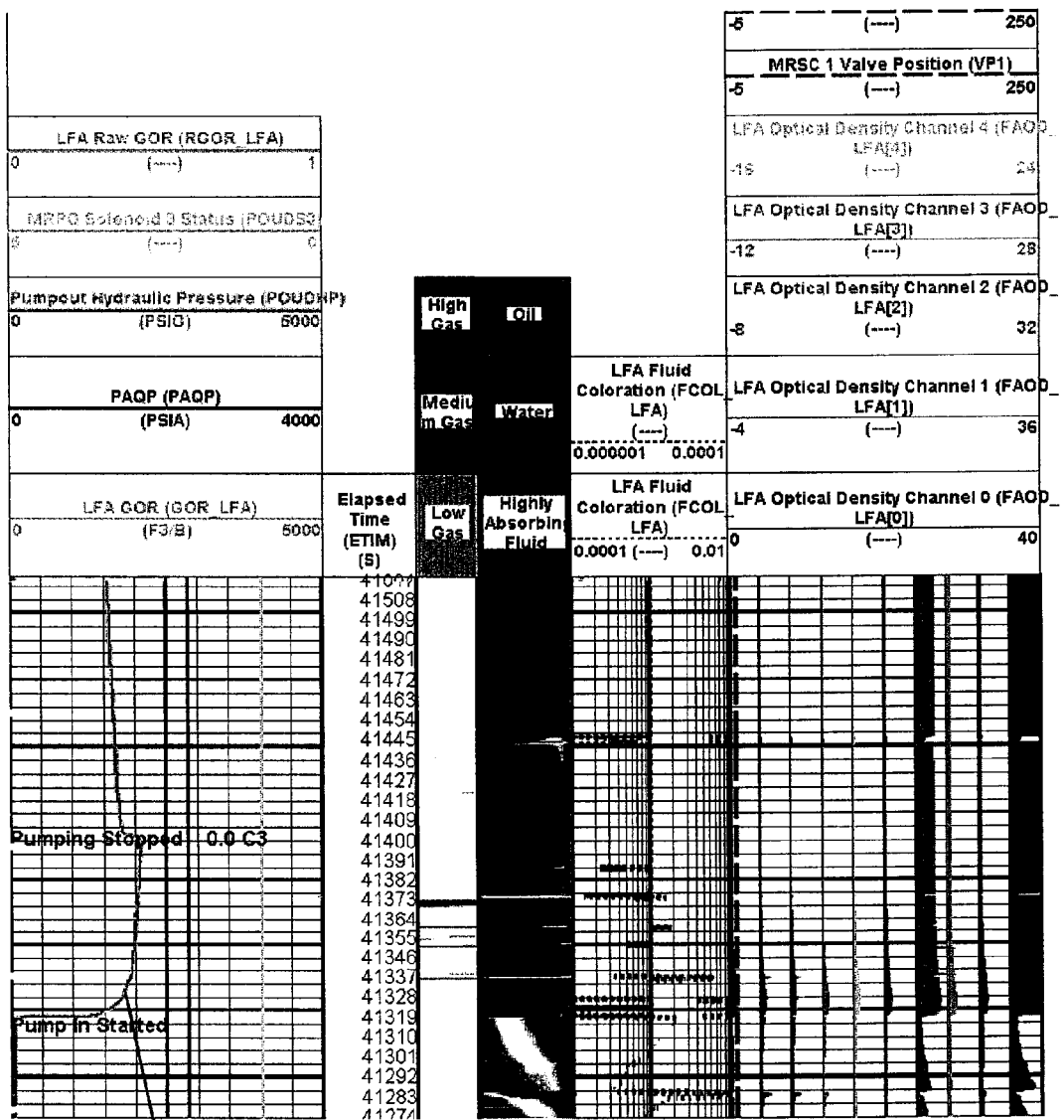
FIG. 6 shows flow line behavior during verification of sample chamber closure.

FIG. 5 shows an example of a sample capture log. On the right (indicated at 500) is the output of the fluid type analyzer. On the left (indicated at 502) is the entry port pressure, pump hydraulic pressure, and pump stroke direction information. FIG. 5 shows that the operator opened the sample chamber correctly (504), caught the desired slug (506), and over-pressured the sample in the sample chamber (508). Note how the pressure ramps up when the sample chamber becomes full (510). Even after the sample chamber is full, pumping continues until the pump reaches maximum compression capability. Once the operator determines that the sample chamber is full, the operator issues a command to close the sample chamber. The operator then verifies that the sample chamber is actually closed. This verification involves closing the exit port (112 in FIG. 1) and then attempting to pump fluids from above the pump (200 in FIG. 1) to below the pump, i.e., from the side of the pump closest to the sample chamber to the other side of the pump. If the sample chamber (122 in FIG. 1) is closed, high resistance is experienced, and the hydraulic pressure of the pump rises rapidly to a maximum allowable value (see pressure curve 600 in FIG. 6). If the sample chamber is open, the pump will be able to push a volume of fluid equal to the volume of the sample chamber before reaching this maximum value.

The invention provides one or more advantages. Using the method and system described above, slugs of individual fluids can be created, and a slug containing a desired fluid can be captured in a sample chamber while slugs containing unwanted fluids can be avoided. This can reduce sampling times in that it is not necessary to wait for the fluid in the flow line to have an acceptable level of contamination before the sample is captured. Whether the sample chamber is successfully opened, sample is captured, and sample chamber is successfully closed can be verified in real time. A record of the capture can be stored for later use. The tool can be constructed using existing formation tester components, such as included in the Schlumberger MDT.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method of sampling reservoir fluid, comprising:
   establishing communication between a reservoir and an entry port of a flow line disposed in a borehole penetrating the reservoir;
   separating fluid received in the entry port into individual fluid components and sequentially flowing slugs of each individual fluid component along the flow line;
   observing the slugs as they move along the flow line in order to determine the composition of the slugs;
   estimating when a desired slug containing a desired fluid component would be in the vicinity of a sample chamber in the flow line; and
   opening the sample chamber to capture the desired slug when the desired slug is in the vicinity of the sample chamber.

2. The method of claim 1, further comprising closing an exit port of the flow line at approximately the same time as opening the sample chamber.

3. The method of claim 1, wherein opening the sample chamber to capture the desired slug comprises pumping the desired slug into the sample chamber.

4. The method of claim 3, wherein pumping the desired slug into the sample chamber comprises pressurizing the content of the sample chamber.

5. The method of claim 1, wherein separating fluid and sequentially flowing slugs comprise passing the fluid received in the entry port through a pump.

6. The method of claim 5, further comprising monitoring a hydraulic pressure of the pump to determine whether opening the sample chamber to capture the desired slug is successful.

7. The method of claim 6, wherein the hydraulic pressure of the pump increases rapidly when the sample chamber becomes full.

8. The method of claim 1, wherein observing the slugs comprises determining whether the slugs contain a single hydrocarbon phase.

9. The method of claim 8, wherein the desired slug contains a single hydrocarbon phase.

10. The method of claim 1, further comprising closing the sample chamber after capturing the desired slug.

11. The method of claim 10, further comprising verifying that the sample chamber is closed by closing an exit port of the flow line and monitoring a hydraulic pressure of a pump in the flow line while attempting to pump fluid from a side of the pump closest to the sample chamber to the other side of the pump, wherein a rapid increase of the hydraulic pressure of the pump indicates that the sample chamber is closed.

12. The method of claim 1, further comprising recording flow conditions at various locations in the flow line and composition of the slugs moving through the flow line, the record being usable for auditing capture of the desired slug.

13. A system for sampling reservoir fluid, comprising:
   a tool body having a flow line with an entry port and an exit port, the tool body being adapted to be suspended in a borehole penetrating a reservoir;
   a fluid separator installed in the flow line for separating fluid received from the entry port into individual fluid components and sequentially outputting slugs of each individual fluid into the flow line;
   a fluid analyzer installed in the flow line downstream of the fluid separator for determining the composition of the slugs as they move along the flow line; and
   at least one sample chamber installed in the flow line downstream of the fluid analyzer for capturing a desired slug containing a desired fluid component.

14. The method of claim 13, wherein the fluid separator is a dual-displacement pump.

* * * * *